United States Patent
Harris

(10) Patent No.: US 10,882,078 B1
(45) Date of Patent: *Jan. 5, 2021

(54) APPARATUS FOR CLEANING AND REMEDIATING ENVIRONMENTAL AIR HANDLING APPARATUS

(71) Applicant: William Edmund Harris, Alpharetta, GA (US)

(72) Inventor: William Edmund Harris, Alpharetta, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/008,592

(22) Filed: Aug. 31, 2020

Related U.S. Application Data

(60) Division of application No. 16/372,065, filed on Apr. 1, 2019, now Pat. No. 10,758,948, and a continuation-in-part of application No. 15/254,933, filed on Sep. 1, 2016, now abandoned.

(51) Int. Cl.
| | |
|---|---|
| *B08B 3/02* | (2006.01) |
| *F28G 15/00* | (2006.01) |
| *F24F 5/00* | (2006.01) |
| *A61L 2/22* | (2006.01) |
| *B08B 9/023* | (2006.01) |
| *F24F 1/06* | (2011.01) |
| *F24F 11/61* | (2018.01) |
| *F28G 9/00* | (2006.01) |

(52) U.S. Cl.
CPC ................. *B08B 3/02* (2013.01); *A61L 2/22* (2013.01); *F24F 5/0035* (2013.01); *F28G 15/003* (2013.01); *B08B 9/023* (2013.01); *F24F 1/06* (2013.01); *F24F 11/61* (2018.01); *F24F 2221/225* (2013.01); *F28G 9/00* (2013.01)

(58) Field of Classification Search
CPC ..... A61L 2/22; A61L 9/14; B08B 3/02; B08B 9/023; F24F 1/06; F24F 5/0035; F24F 11/61; F24F 2221/225; F24G 1/166; F24G 3/166; F28G 9/00; F28G 15/003
See application file for complete search history.

(56) References Cited

U.S. PATENT DOCUMENTS

| | | | | |
|---|---|---|---|---|
| 4,780,333 A | * | 10/1988 | Smith ................. | A61L 2/22 427/236 |
| 5,737,937 A | * | 4/1998 | Akazawa ............. | A61L 9/14 62/303 |

(Continued)

*Primary Examiner* — Eric S Ruppert
*Assistant Examiner* — Hans R Weiland
(74) *Attorney, Agent, or Firm* — Sanford Jay Asman

(57) ABSTRACT

The present invention is directed to systems for cleaning a component inside a machine, such as an evaporator coil inside an air conditioner. A pump is connected to a controlling device. The pump is also connected to a metering device. The metering device is connected to one or more reservoirs. The metering device is also connected to one or more devices, adapted to generate a fog whose particles have a mean diameter of less than about 15 microns. To perform the cleaning of the component, the controlling device disables the machine. The controlling device then activates the pump. The pump causes cleaning solution to be drawn from the one or more reservoirs into the metering device, which then transfers the cleaning solution into the fog generating device(s). The controlling device then allows the machine to resume operation.

9 Claims, 8 Drawing Sheets

(56) References Cited

U.S. PATENT DOCUMENTS

| | | | | |
|---|---|---|---|---|
| 6,656,434 | B1* | 12/2003 | DeMarcki | A61L 9/14 422/116 |
| 10,758,948 | B1* | 9/2020 | Harris | F28G 15/003 |
| 2003/0056812 | A1* | 3/2003 | Baker | B08B 3/02 134/36 |
| 2005/0135976 | A1* | 6/2005 | Sagar | A61L 9/14 422/124 |
| 2006/0037330 | A1* | 2/2006 | Weigl | A61L 9/14 62/78 |
| 2007/0125520 | A1* | 6/2007 | Nutsos | F28G 9/00 165/95 |
| 2008/0283626 | A1* | 11/2008 | Aldana | A61L 9/14 239/68 |
| 2009/0000317 | A1* | 1/2009 | Schill | F28G 9/00 62/78 |
| 2013/0255285 | A1* | 10/2013 | Kocher-Kunz | A61L 9/14 62/78 |
| 2017/0028449 | A1* | 2/2017 | Fernholz | B08B 3/02 |
| 2017/0197000 | A1* | 7/2017 | Buzzi | F28G 9/00 |

\* cited by examiner

PRIOR ART
FIG. 2
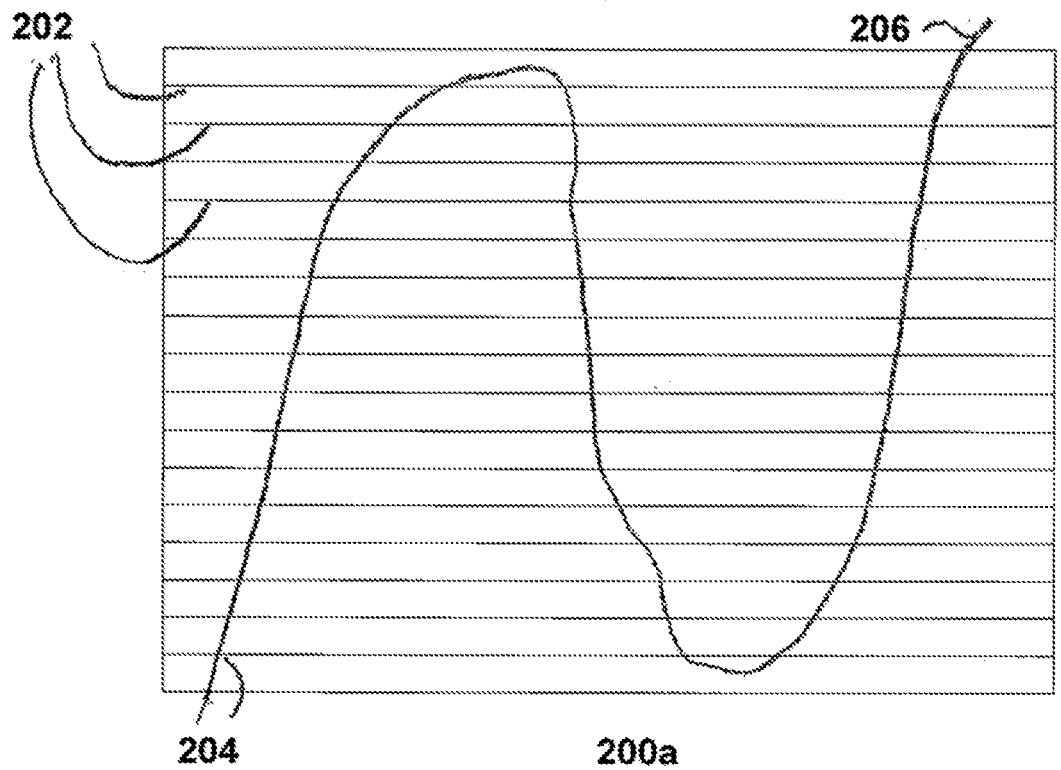
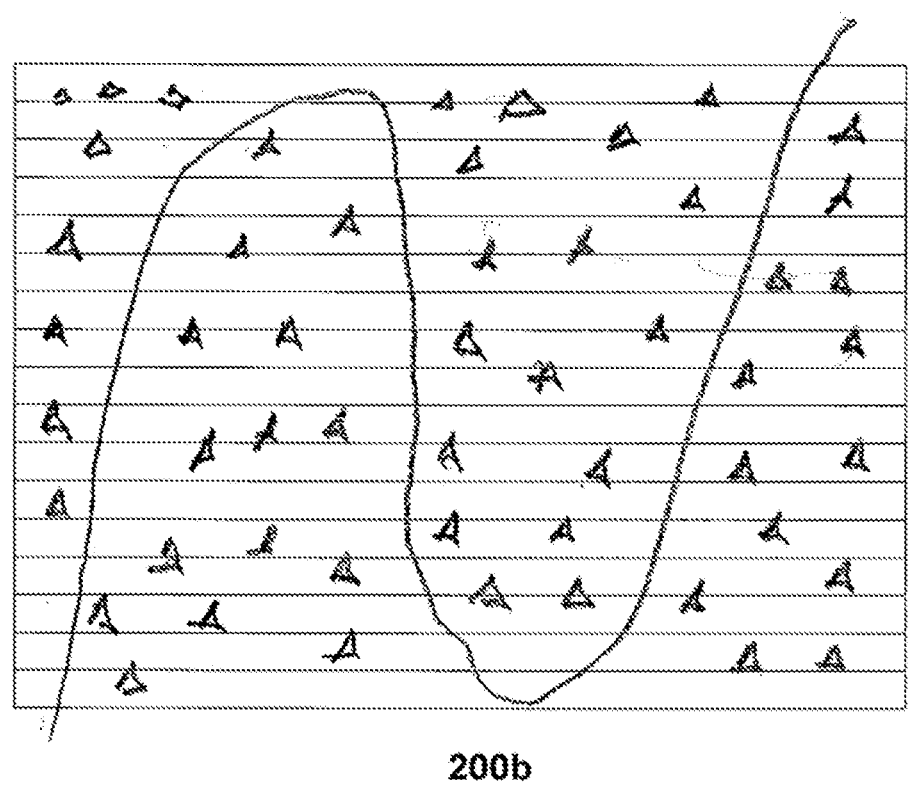

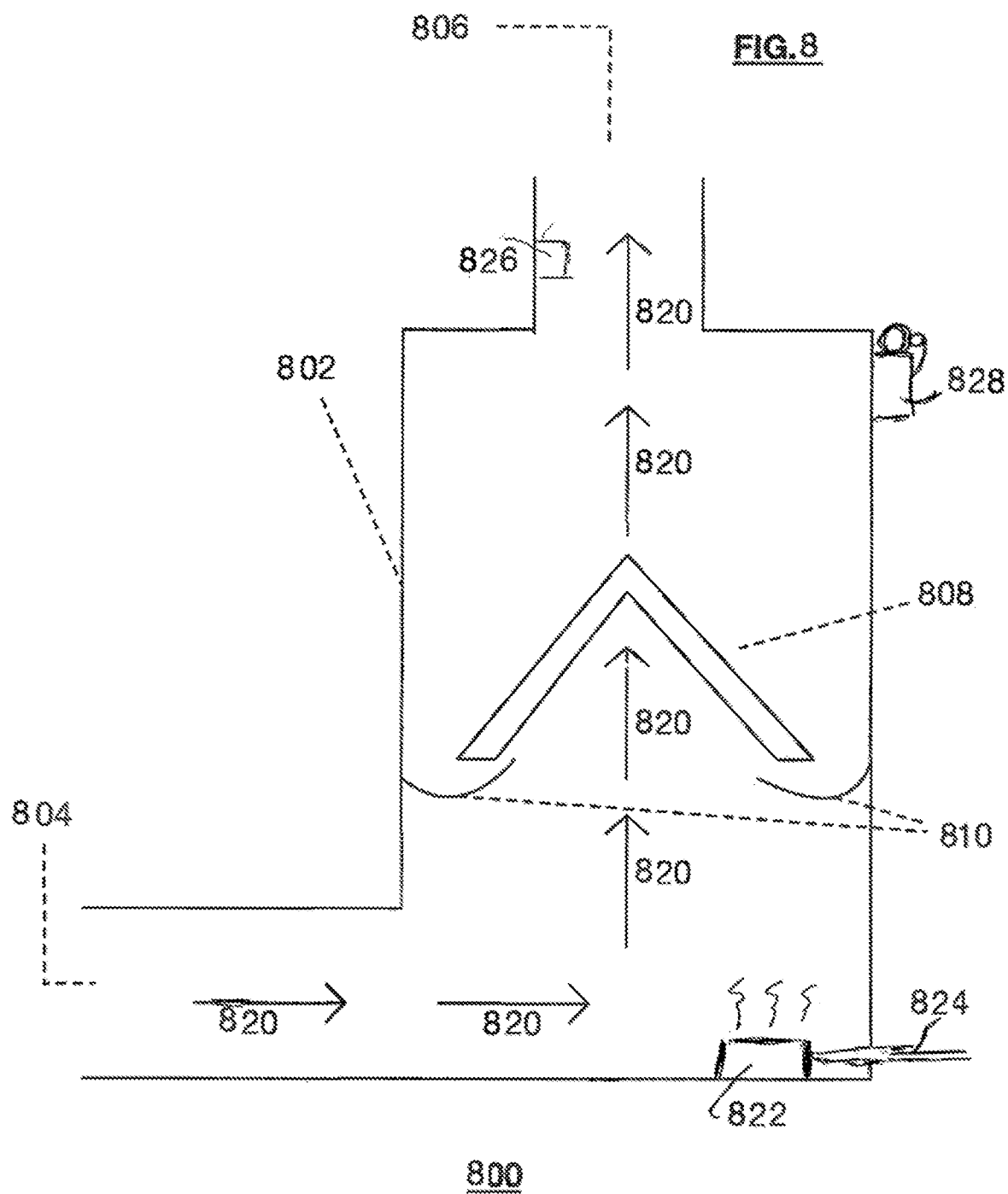

APPARATUS FOR CLEANING AND REMEDIATING ENVIRONMENTAL AIR HANDLING APPARATUS

CROSS-REFERENCE TO RELATED APPLICATION(S)

The present application is a divisional of U.S. patent application Ser. No. 16/372,065 filed Apr. 1, 2019 now U.S. Pat. No. 10,758,065 issued Sep. 1, 2020 which was a continuation-in-part of U.S. Ser. No. 15/254,933, filed Sep. 1, 2016 entitled SYSTEM AND METHOD FOR AIR CONDITIONER EVAPORATOR COIL CLEANING.

BACKGROUND OF THE INVENTION

The present invention is generally directed to apparatus and methods for cleaning and remediating environmental air handling equipment. In particular, the present invention may be used to improve the operation of air conditioners and similar pieces of air handling equipment, and is more particularly directed to methods and systems of cleaning an evaporator coil and the other internal portions of the equipment while the equipment is in service.

While the present invention relates to a variety of air handling equipment, for the purpose of this application reference will be made to air conditioners. However, it should be understood that such reference is intended to be solely directed to a specific piece of air handling equipment while the present invention is generic to all such equipment.

In the case of air conditioners, it is common to cool air through the use of an evaporator coil housed inside the plenum of the air conditioner. Evaporator coils draw moisture from the air being cooled, in the form of condensation. Because evaporator coils are located inside the plenum, they are not exposed to light. The dark, wet environment inside the plenum, as well as the associated ductwork, provide an ideal environment for the growth of mildew. Accordingly, it is common for mildew to grow on the surfaces of evaporator coils. Because air flows over the evaporator coil while the air conditioner is operating, air is also flowing over the accumulated mildew. Sufficient mildew buildup can cause the air conditioner to operate at reduced efficiency, because less air is able to flow over the coil in a given amount of time. In some cases, the mildew buildup is sufficient to cause a strain on the air conditioner motor, causing other repairs to be necessary. In extreme cases, mildew also grows in the path for condensation to leave the building, causing a backup of condensation to occur, which can lead to leaks and flooding inside the building. In fact, it is not uncommon for such condensate backup to result in leaks through the ceilings when an air conditioner is mounted in an attic. Sufficient levels of mildew can also make the air unhealthy to breathe, because microscopic amounts of mildew are blown away from the evaporator coil by the airflow, allowing the mildew to flow freely in the circulated air and to grow inside of the ductwork, as well.

Existing systems for cleaning evaporator coils involve removing a panel from the plenum and spraying a cleanser on the evaporator coil or completely removing the evaporator coil for a more thorough cleaning. These systems are time consuming and require human interaction. Accordingly, evaporator coils are not cleaned often. In some cases, the evaporator coils may not be cleaned, if at all, until there is a problem with air quality, a leak due to condensate backup, or some other problem with the operation of the air conditioner.

SUMMARY OF THE INVENTION

To address the problems stated above, it is desirable to have a cleaning system that cleans the evaporator coil and the internal portions of the air handling system before a build-up of mildew occurs. Such a system would allow air conditioners to operate more efficiently, because the flow of air would not be impeded by mildew on the evaporator coil. Such a system would also allow for a lower cost of repairs because the air conditioner would not break down due to the buildup of mildew. Such a system would also prevent costly repairs due to leaks or flooding caused by a mildew buildup inside the drainage system for air conditioner condensation, which could lead to fewer insurance claims being filed. Such a system would also lead to healthier air quality inside the building, because the air would not be contaminated by mildew buildup inside the air conditioner. Such a system could also be used to clean components in other types of air handling apparatus.

This brief overview is provided to introduce a selection of concepts in a simplified form that are further described hereinafter, whereby this brief overview is not intended to identify key features or essential features of the claimed subject matter. Nor is this brief overview intended to be used to limit the scope of the present invention.

The present invention is directed to systems and methods for cleaning components of air handling apparatus, such as an evaporator coil inside an air conditioners, while the apparatus remains in service. The systems described can be retrofitted in air handling apparatus that is already installed in a building. Alternatively, the systems described can also be incorporated into air handling apparatus before it is installed in a building.

In one embodiment of the present invention, wands may be located inside the plenum of an air conditioner with the wands having nozzles directed at the face of the evaporator coil. The ingredients for the cleaning solution may be drawn from one or more reservoirs, and delivered by a metering type pump. A controlling device that is also able to turn the air conditioner off for the duration of the cleaning cycle may control the pump. The system may operate on a cycle, as is often warranted by the size of the evaporator coil and the volume of air being handled by the air conditioner. The reservoirs can be refilled or replaced as needed.

The system may operate by disabling the air conditioner for a period of time. The system may then mechanically or electronically spray a cleaning solution onto the face of the evaporator coil inside the air conditioner using the described system. The system may then wait a period of time for the cleaning solution to work. The system may then re-enable the air conditioner so it can resume normal operations.

In other embodiments of the invention, it has been found to be desirable to introduce a "fog" generated by a nebulizer, rather than by using a spray. As used herein the term "fog" is intended to distinguish from a spray in that the particles of a fog are generally considered to be less than 50 microns in diameter, whereby they will remain suspended in the air until they condense on a portion of the air handling apparatus (e.g., on the evaporator coil or inside of the plenum or ductwork) or they evaporate. As will be understood by those skilled in the art, a device, such as a nebulizer, rather than a spray nozzle, is used to generate a fog. By way of example, an ultrasonic nebulizer can be used to create a fog of the type used in the present invention.

Both the foregoing brief overview and the following detailed description provide examples and are explanatory only. Accordingly, the foregoing brief overview and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF THE DRAWING

In the drawings:

FIG. 2 is one embodiment of the face of a typical evaporator coil used in an air conditioning system;

FIG. 8 illustrates yet another embodiment of the invention in which various types of air sensors, solution-dispensers, and alarms may be used in combination with the computer system shown in FIG. 7, to provide data, remediation, alarms, etc.

DETAILED DESCRIPTION OF THE PREFERRED EMBODIMENTS

Figure 1:
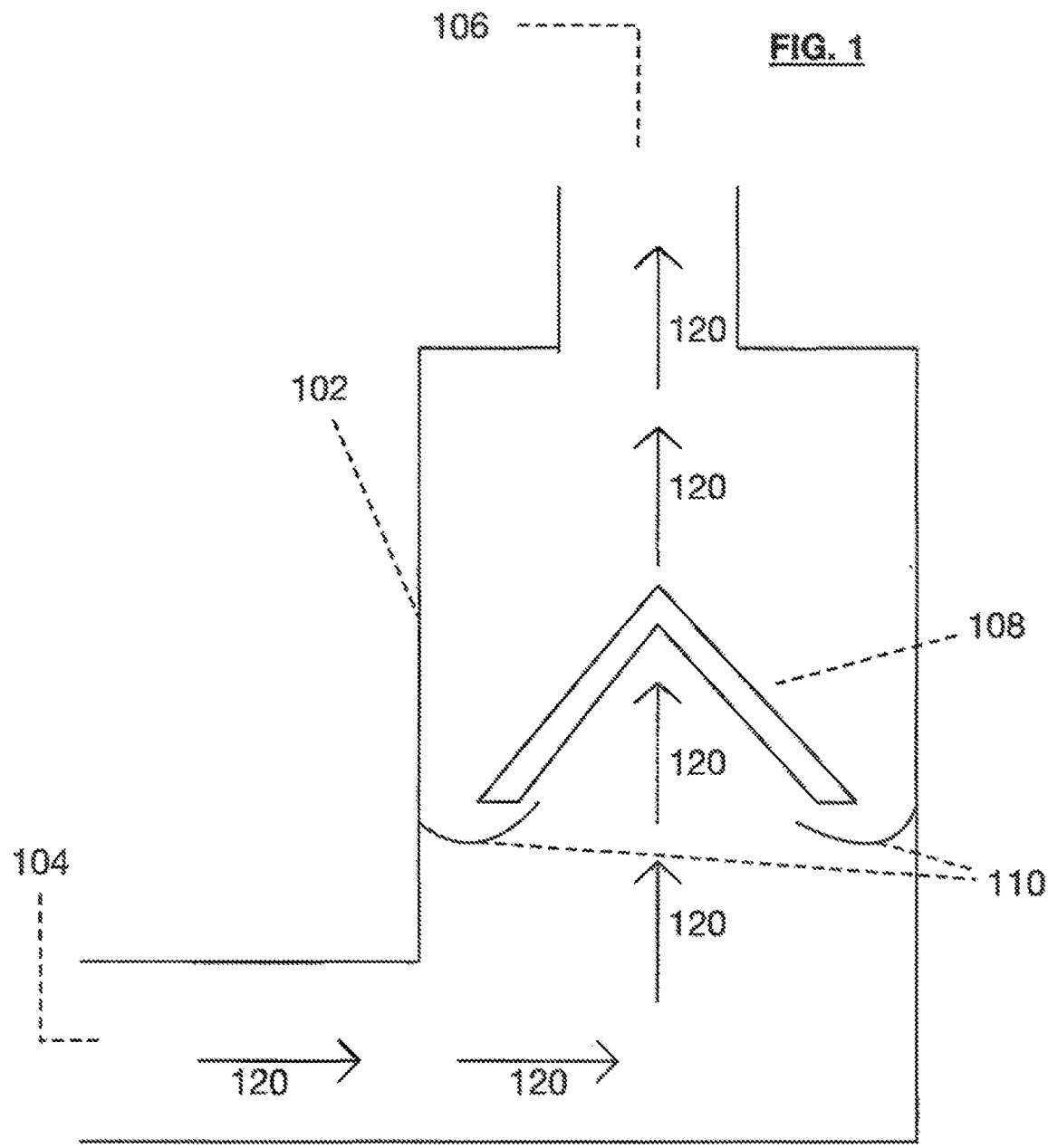
FIG. 1 is one embodiment of an air-handling unit in a typical air conditioning system.

In a first embodiment of the invention, the evaporator coil cleaning system is integrated into a machine, such as an air conditioning system, so that it can run on a schedule without human intervention. At certain intervals, the cleaning system powers down the machine, sprays cleaning solution onto the component(s) to be cleaned, waits a period of time for the cleaning solution to work, and then powers up the machine, allowing normal operations to resume.

As a preliminary matter, it will readily be understood by one having ordinary skill in the relevant art that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the embodiments of the present invention. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present invention.

Accordingly, while embodiments are described herein in detail in relation to one or more embodiments, it is to be understood that this disclosure is illustrative and exemplary of the present invention, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein, as understood by the ordinary artisan based on the contextual use of such term, differs in any way from any particular dictionary definition of such term, it is intended that the meaning of the term as understood by the ordinary artisan should prevail.

Furthermore, as used herein, "a" and "an" each generally denotes "at least one," but does not exclude a plurality unless the contextual use dictates otherwise. When used herein to join a list of items, "or" denotes "at least one of the items," but does not exclude a plurality of items of the list.

Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the invention may be described, modifications, adaptations, and other implementations are possible. For example, substitutions, additions, or modifications may be made to the elements illustrated in the drawings, and substituting, reordering, or adding stages to the disclosed methods may modify the methods described herein. Accordingly, the following detailed description does not limit the invention. Instead, the proper scope of the invention is defined by the appended claims.

The present invention includes many aspects and features. Moreover, while many aspects and features relate to, and are described in, the context of cleaning the evaporator coil of an air conditioner while it is in service, embodiments of the present invention are not limited to use only in this context and can be used to clean any component of any machine.

With reference to the prior art illustrated in FIG. 1, embodiments of the present invention can be retrofitted into, but not limited to, an air handling unit 100 of a conventional air conditioner system. The system illustrated in FIG. 1 is just one embodiment of an air-handling unit in a typical air conditioning system compatible with the systems and methods described herein. Further still, embodiments of the present invention can be manufactured and sold as an integrated air conditioning system. The air conditioning system 100 can be any type of air conditioner system that cools air with the use of an evaporator coil. Air conditioning system 100 can be installed in a residential or commercial building.

FIG. 1 depicts airflow using arrows 120. For example, air enters a plenum 102 through the return 104 and exits plenum 102 through a supply 106. The plenum 102 houses an evaporator coil 108. Evaporator coil 108 is a so-called A-coil. The examples described herein can also be used with other types of evaporator coils, including, but not limited to slant coils, H coils, or other types of coils. Condensation accumulating on the coil 108 during the cooling process is intended to drain into channels 110, which are intended to direct the accumulated condensate to a safe place, usually outside the building, through a system of pipes (not shown) and which may include a condensate pump (not shown). In some embodiments, a drain pan (not shown) may be used to direct the condensate outside the building.

FIG. 2 illustrates an embodiment of the face of a typical evaporator coil used in an air conditioning system, before (shown at 200a) and after (shown at 200b) it is clogged with mildew. In various embodiments, fins 202 may be arranged in rows roughly parallel to each other. The coolant enters the evaporator coil from a compressor (typically located outside of the structure whereby it can dissipate heat) through a pipe or tube at an entrance 204, with the pipe or tube shaped to direct the coolant throughout the evaporator coil. The coolant may exit the evaporator coil at an exit 206 and be directed back to the external compressor. Over time, mildew may accumulate on and between fins 202 of the evaporator coil. In the depictions illustrated in FIG. 2, the spaces between the fins 202 of the evaporator coil face 200a are clean and the spaces between the fins 202b of evaporator coil face are clogged with mildew, as demonstrated by the shading in 200b.

Figure 3:
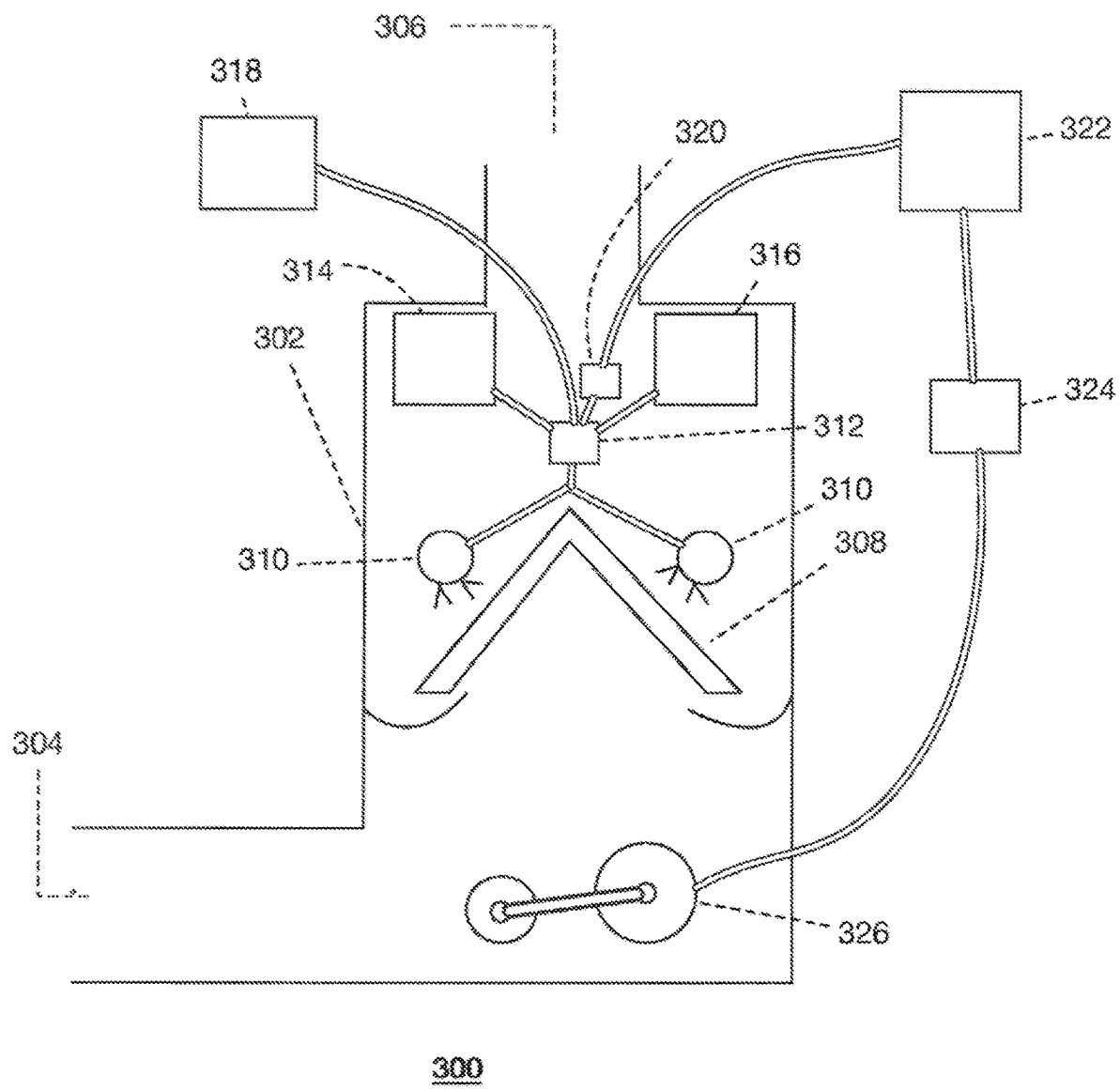
FIG. 3 is one embodiment of a system consistent with embodiments of the present invention.

FIG. 3 is first embodiment of a system 300 consistent with the present invention. Plenum 302 houses the evaporator coil 308 and part of the cleaning system. Consistent with embodiments of the present invention, air may enter the plenum 302 at the return 304. The air is directed across, and through, the evaporator coil 308, and it exits at the supply 306. In a first embodiment of the invention, wands 310 are placed inside the plenum 300 roughly parallel to each face of the evaporator coil. The wands 310 may be of a length and diameter suitable to be able to spray cleaning solution along the entire face of the coil. Notably, unlike the sprayers used in the prior art, the wands include nozzles that cause cleaning solution to be sprayed over the entire surface of the evaporator coil 308, rather than "dripping" the cleaning solution onto the evaporator coil 308. In particular, it is intended that the cleaning solution be sprayed, rather than flowed (as a "waterfall") over the entire surface of the evaporator coil 308.

The wands 310 are connected to a metering device 312 using tubing or pipe. The metering device 312 may be mechanically or electronically controlled to cause an appropriate amount of the various components of the cleaning solution to enter the wands 310 and be sprayed on the evaporator coil 308. The components of the cleaning solution may be taken from a first reservoir 314, a second reservoir 316, and a water system 318. In some embodiments, it is desirable to store the components of the cleaning solution in different reservoirs because the cleaning solution will break down if the components are mixed before the cleaning solution is used. However, non-reactive components may be premixed, reducing the number of reservoirs needed and other components may be added to the cleaning solution, increasing the number of reservoirs needed beyond the two 314, 316 illustrated. The reservoirs 314, 316 may be attached to the exterior of the plenum 302 or hung at an appropriate height nearby. An appropriate height could be any height that allows a pump 320 to cause the reservoir contents to enter the metering device 312. The reservoirs containing the components of the cleaning solution may be refillable or replaceable. In a typical residential installation, replacement reservoirs may be attached to the tubing or piping leading to the metering device after an empty reservoir is removed. Any currently existing system of removing and attaching the reservoirs may be used. Refillable reservoirs may also be removable, for the purpose of refilling them.

The water system 318 may be any system that supplies water to the metering device 312. For example, the water system 318 may be a reverse osmosis filtration system that is connected to the building plumbing. In some embodiments, the water system 318 may draw water from the building plumbing, run it through the reverse osmosis filtration, and supply the filtered water to the metering device 312. It is also foreseeable that in cases where the water supply cannot be connected to plumbing, the water system 318 may be a tank of purified water.

Because the cleaning solution is being used in a system that supplies air to the building, occupants of the building may inhale fumes from the cleaning solution. It is therefore desirable for the cleaning solution to be non-toxic and organic. However, the system is operable with any type of solution that will kill and break down mildew. In some embodiments, one reservoir stores hydrogen peroxide and a second reservoir stores a blend of organic cleansing agents. By way of example, the blend of organic cleansing agents may be a mixture of grapefruit seed extract and orange oil. The hydrogen peroxide acts as a fizzing agent, while the grapefruit seed extract acts as the working ingredient that operates to kill any mildew that has started to grow and breaks it down so that it will be rinsed away during the cleaning process, the orange oil acts as a surfactant, and the water acts as the carrier. Other combinations of ingredients may be used, with the appropriate number of reservoirs incorporated into the system.

With continued reference to FIG. 3, the metering device 312 may be connected to pump 320 using tubing or pipe so that pump 320 can cause the metering device 312 to draw fluid from the reservoirs 314, 316. Pump 320 may be connected to a controlling device 322. The controlling device 322 may be programmed with the time and duration for the cleaning system to run. The controlling device 322 may be configurable via a user interface. The controlling device 322 may also be connected to the air conditioner controls 324, which may in turn be connected to the air conditioner blower motor 326. The controlling device 322 may ensure that the cleaning system and the air conditioner will not operate at the same time by turning off the air conditioner when the cleaning system is about to run. Turning off the air conditioner may prevent the cleaning solution from being blown about inside the plenum 302 and instead allows for the cleaning solution to reach the evaporator coil 308. The controlling device 322 also may prevent the air conditioner from powering on until an amount of time has passed for the cleaning solution to kill and break down the mildew. After the appropriate amount of time has passed, the controlling device 322 may stop preventing the air conditioner from powering on, so that the air conditioner may once again be operated by the air conditioner controls 324.

The frequency of the operation of the cleaning system, the length of time the cleaning system runs, and the amount of time allowed for the cleaning solution to work before the air conditioner continues normal operations may vary according to the size of the coil being cleaned and the amount of air being handled by the air conditioner. Other factors may be considered. These time periods would typically be set at the factory, but may be configurable onsite, through the use of the controlling device 322. In one example, the controlling device 322 may disable the air conditioner and operate the cleaning system once every seventy-two hours, the cleaning system may run for thirty seconds, and the controlling device 322 may keep the air conditioner from powering back on for five minutes.

Figure 4:
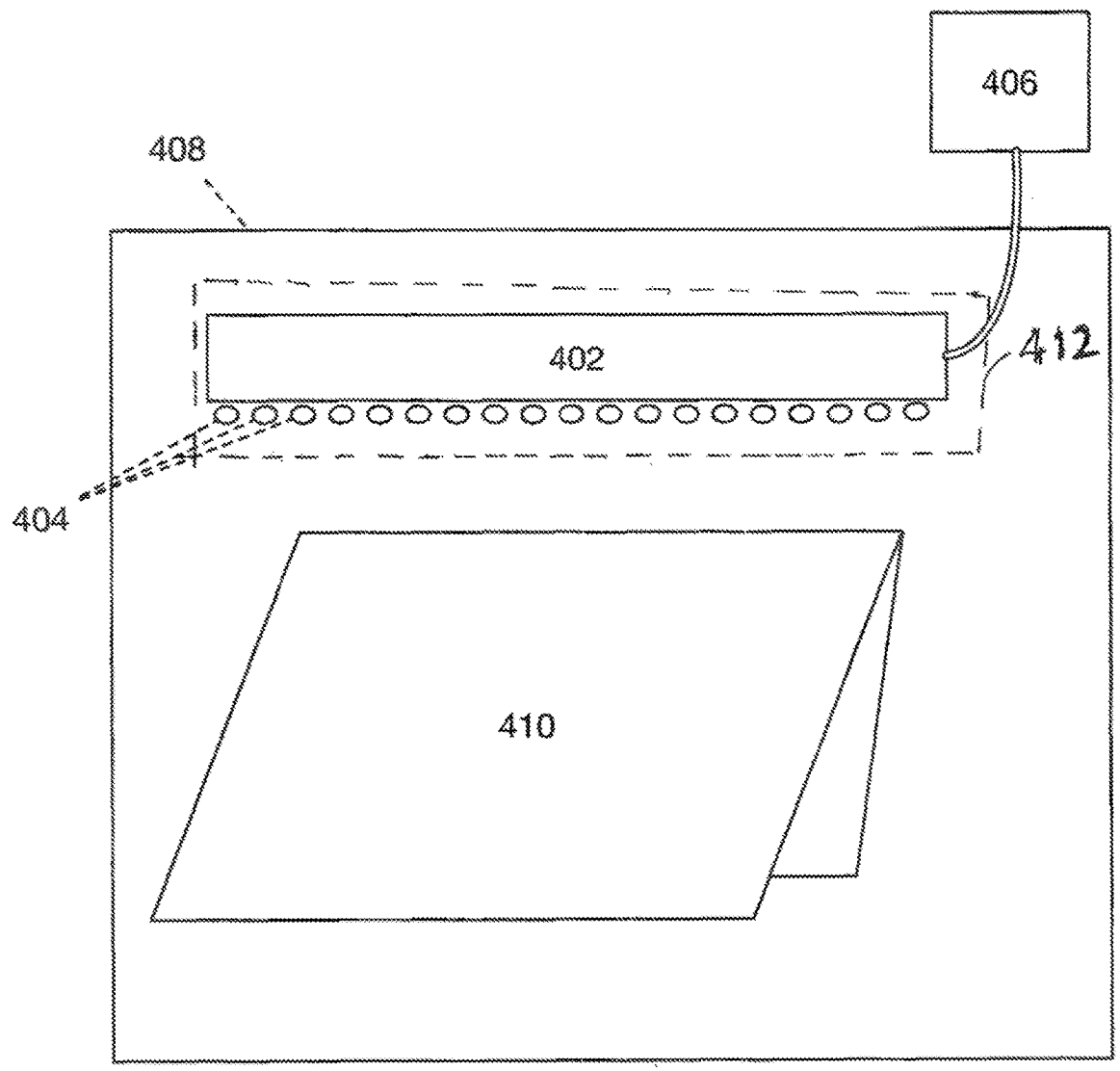
FIG. 4 illustrates a side view of an embodiment of the evaporator coil and the wand.

Referring to FIG. 4, a side view of some embodiments of the evaporator coil and the wand is illustrated. FIG. 4 depicts just one face 410 of the evaporator coil and the wand 412 used to clean it, all of which are housed inside the plenum 408. Each wand 412 may comprise a tube 402 and multiple nozzles 404. Each wand 412 may be connected to a metering device 406 using tubing or pipes that extend through the wall of the plenum 408, and metering device 406 may then, in turn, be connected to the rest of the system as described above with reference to FIG. 3. When wand 412 is activated, each nozzle 404 may spray cleaning solution onto a portion of evaporator coil 410, such that the cleaning solution from the nozzles 404 overlap with the cleaning solution from the neighboring nozzles such that the entire surface area of the face 410 of the evaporator coil is sprayed with cleaning solution. Again, when cleaning solution is sprayed onto the face of the evaporator coil 410 it is intended that such spray covers the entire face of the evaporator coil 410 without need for "dripping" or "water falling", as was the case with systems heretofore used. Excess cleaning solution may drain into the system used to collect the condensate from the evaporator coil 410 and direct it to an appropriate place.

When the cleaning system is activated, metering device 406 may feed cleaning solution into wand 412. Within the wand 412, cleaning solution may travel through the tube 402 and may exit tube 402 through each of multiple nozzles 404. After exiting through each of multiple nozzles 404, cleaning solution may travel through the air towards evaporator coil 412 and land on evaporator coil 412.

Figure 5:
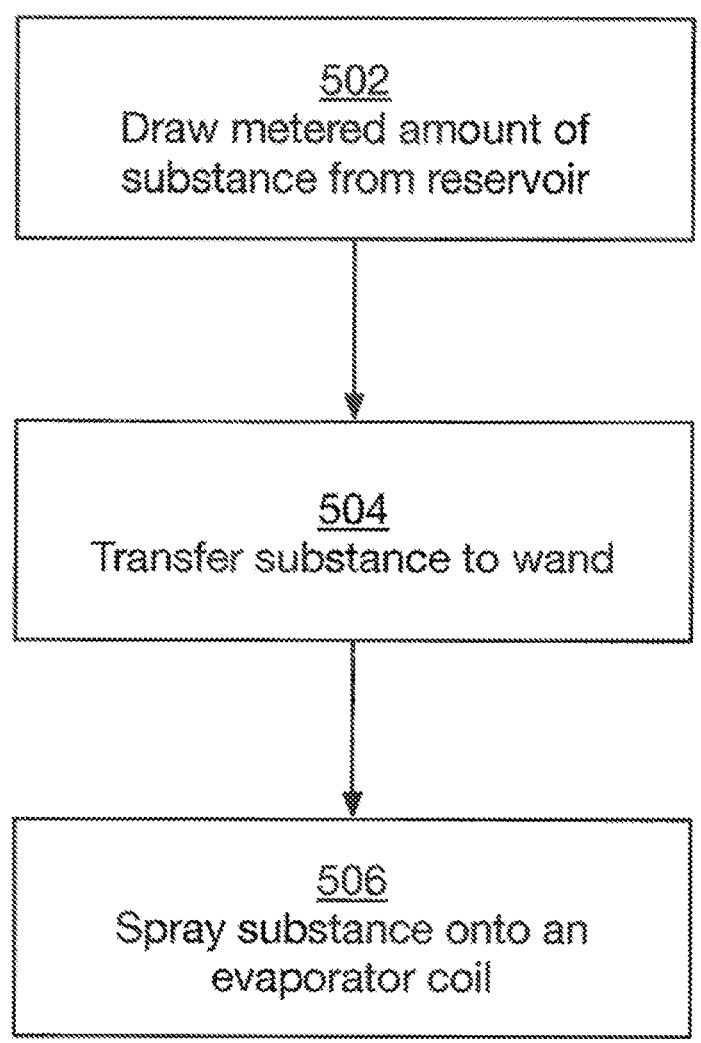
FIG. 5 illustrates a flow chart for performing a method for operating an embodiment of an evaporator coil cleaning system in accordance to an embodiment of the present invention.

FIG. 5 illustrates a flow chart setting forth the general stages involved in a method 500 consistent with some embodiments of the invention. Method 500 may be implemented using a computing device.

Although the steps, or stages, illustrated by the flow charts are disclosed in a particular order, it should be understood that the order is disclosed for illustrative purposes only. Stages may be combined, separated, reordered, and various intermediary stages may exist. Accordingly, it should be understood that the various stages illustrated within the flow chart might, in various embodiments, be performed in arrangements that differ from the ones illustrated. Moreover, various stages may be added to or removed from those illustrated in the flow charts without altering or deterring from the fundamental scope of the depicted methods and systems disclosed herein. Ways to implement the stages of method 500 will be described in greater detail below.

Method 500 may begin at starting block 502 and proceed to stage 506. For example, in step 502, the controlling device may operate a pump to draw a metered amount of substance from a reservoir. Following step 502, the controlling device may advance to stage 504 wherein a pump may be employed to transfer the metered amount of substance to the wand. The wand is positioned to spray the metered amount of substance onto the evaporator coil as illustrated in FIG. 4. Following step 504, the controlling device may advance to step 506, wherein the metered amount of substance is sprayed through the nozzles on the wand onto the evaporator coil. Once the controlling device has completed stage 506, method 500 may end.

Figure 6:
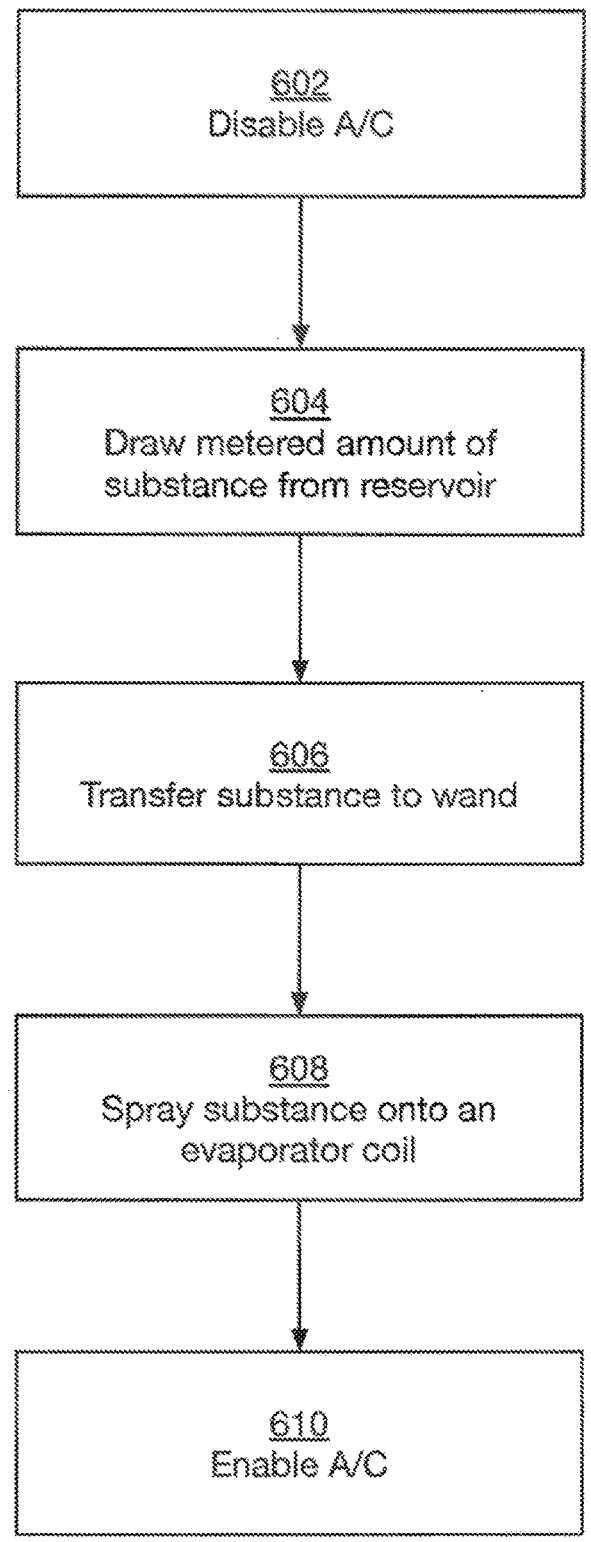
FIG. 6 illustrates a flow chart for performing a method for operating an embodiment of an evaporator coil cleaning system in accordance to another embodiment of the present invention.

With reference to FIG. 6, method 600 may begin at starting block 602 and proceed to stage 610 where a controlling device may disable the air conditioner from operating while the cleaning system is operating. For example, in step 602, the controlling device may be a computing device that disables the air conditioner. For example, the controlling device may override the air conditioner controls and prevent the air conditioner from cycling on. The controlling device may accomplish this in a number of ways, including cutting power to the air conditioner or entering a temperature value into a thermostat that is higher than an operational thermostat setting. Other ways of preventing the air conditioner from cycling on can be envisioned. The controlling device may also be a mechanical device, such as a timer or other device connected to the thermostat. The mechanical controlling device may have a user interface that, for example, allows a user to move slider or dial controls to set the time to perform a cleaning cycle, the length of time for the cleaning cycle to run, the length of time for the air conditioner to be disabled, or the thermostat value that is used to disable the air conditioner. From step 602, the controlling device may advance to step 604.

In step 604, the controlling device may cause the pump to draw a metered amount of substance from the reservoir. Next, at step 606, the pump may transfer the metered amount of substance to the wand. From step 606, the controlling device may advance to step 608, wherein the cleaning substance is sprayed through the wand onto the evaporator coil. From step 608, the controlling device may advance to step 610, wherein the controlling device may re-enable the air conditioner, such that it can continue to operate via the air conditioner controls. For example, the controlling device may enable the air conditioner by reversing the action taken in 602. Once the controlling device has completed stage 610, method 600 may end.

Although methods 500 and 600 have been described in some embodiments to be performed by a computing device (e.g., computing device 700 described with reference to FIG. 7, it should be understood that in some embodiments different operations may be performed by different networked elements in operative communication with the computing device. For example, a server and/or a local computing device may be employed in the performance of some or all of the stages in methods 500 and 600. Moreover, the server may be configured much like the computing device and, in some instances, be one and the same embodiment. Similarly, a local controlling device may be employed in the performance of some or all of the stages in methods 500 and 600. A controlling device may also be configured much like a computing device.

Aspects of the present invention may be implemented using any material suitable for the amount of pressure exerted on the system and in various configurations with the parts connected in any manner. The system may be controlled electronically, wirelessly, or using a combination of electronic and wireless communications using any suitable communication protocol. The system may be part of a network of appliances installed according to the Internet of Things (often referred to as "IoT"). The system may include an input device configured to accept input corresponding to the frequency and duration of the operation of the system. The system may include an input device configured to output supply levels or present the results of the system operations to the user. A computing device may be used in the implementation of the various embodiments described here.

Figure 7:
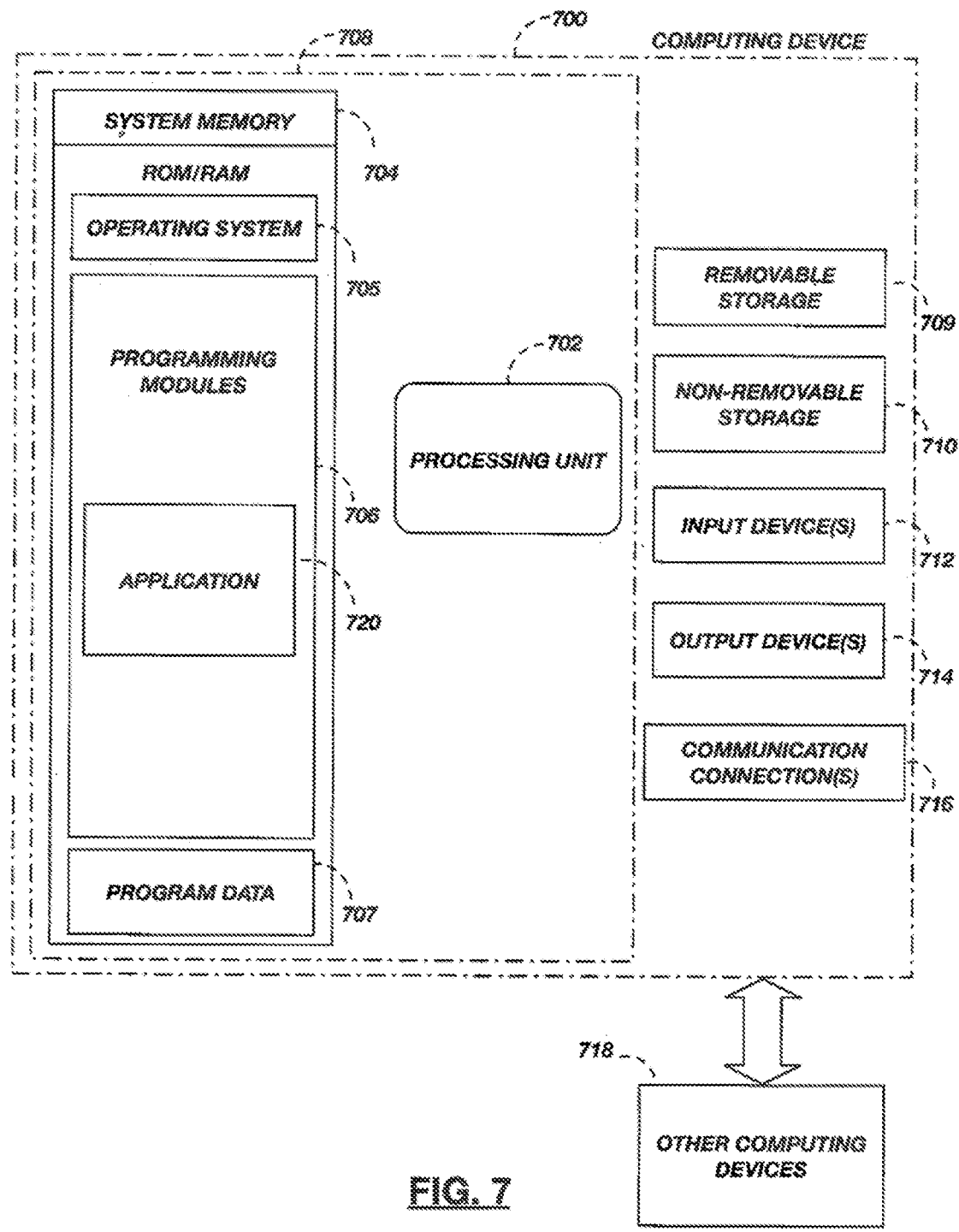
FIG. 7 illustrates a block diagram of a computer system used with the present invention.

FIG. 7 is a block diagram of a system including computing device 700. Consistent with an embodiment of the present invention, a memory storage and processing unit may be implemented in a computing device, such as computing device 700 of FIG. 7. Any suitable combination of hardware, software, or firmware may be used to implement the memory storage and processing unit. For example, the memory storage and processing unit may be implemented with computing device 700 or any of other computing devices 718, in combination with computing device 700. The aforementioned system, device, and processors are examples and other systems, devices, and processors may comprise the aforementioned memory storage and processing unit, consistent with embodiments of the invention.

With reference to FIG. 7, a system consistent with an embodiment of the invention may include a computing device, such as computing device 700. In a basic configuration, computing device 700 may include at least one processing unit 702 and a system memory 704. Depending on the configuration and type of computing device, system memory 704 may comprise, but is not limited to, volatile (e.g., random access memory (RAM)), non-volatile (e.g., read-only memory (ROM)), flash memory, or any combination. System memory 704 may include an operating system 705, one or more programming modules 706, and it may include program data 707. Operating system 705, for example, may be suitable for controlling the operation of computing device 700. In one embodiment, programming modules 706 may include a timing module that controls the frequency and the duration of the cleaning cycle, a pump operation module that controls the amount of fluid drawn from each reservoir, and a machine control module that disables the machine containing the component during the cleaning cycle.

Furthermore, embodiments of the invention may be practiced in conjunction with a graphics library, other operating systems, or any other application program and is not limited to any particular application or system. This basic configuration is illustrated in FIG. 7 by those components within a dashed line 708.

Computing device 700 may have additional features or functionality. For example, computing device 700 may also include additional data storage devices (removable and/or non-removable) such as, for example, magnetic disks, optical disks, or tape. Such additional storage is illustrated in FIG. 7 by a removable storage 709 and a non-removable storage 710. Computer storage media may include volatile and nonvolatile, removable and non-removable media implemented in any method or technology for storage of information, such as computer readable instructions, data structures, program modules, or other data. System memory 704, removable storage 709, and non-removable storage 710 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 700. Any such computer storage media may be part of device 700. Computing device 700 may also have input device(s) 712 such as a keyboard, a mouse, a pen, a sound input device, a touch input device, etc. Output device(s) 714 such as a display, speakers, a printer, etc. may also be included. The aforementioned devices are examples and others may be used.

Computing device 700 may also contain a communication connection 716 that may allow device 700 to communicate with other computing devices 718, such as over a network in a distributed computing environment, for example, an intranet or the Internet, whereby "home automation" controls may be incorporated, as well, and they may allow for control from remote locations, e.g., via a smartphone application. Communication connection 716 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media. As stated above, a number of program modules and data files may be stored in system memory 704, including operating system 705. While executing on processing unit 702, programming modules 706 may perform processes including, for example, one or more of drawing a metered amount of substance from a reservoir, transferring the substance to a wand, or spraying the substance onto an evaporator coil as described above. The aforementioned process is an example, and processing unit 702 may perform other processes. Other programming modules that may be used in accordance with embodiments of the present invention may include air conditioning controls, user interface applications, etc.

Referring now to FIG. 8, yet another embodiment 800 of the invention is described. In the embodiment 800, airflow is depicted by arrows 820. As in the embodiment shown in FIG. 1, air enters a plenum 802 through the return 804 and exits plenum 802 through a supply 806. The plenum 802 houses an evaporator coil 808. Evaporator coil 108 is a so-called A-coil. The examples described herein can also be used with other types of evaporator coils, including, but not limited to slant coils, H-coils, or other types of coils. Condensation accumulating on the coil 808 during the cooling process is intended to drain into channels 810, which are intended to direct the accumulated condensate to a safe place, usually outside the building, through a system of pipes (not shown) and which may include a condensate pump (not shown). In some embodiments, a drain pan (not shown) may be used to direct the condensate outside the building.

The embodiment 800 further includes at least one solution-dispensing device 822. While only one such device is shown, two or more may be employed. Unlike the other embodiments previously shown, it is intended that each solution-dispensing device 822 include means for generating a fog or means for atomizing a solution. As used herein, the term "fog" is intended to mean a distribution of solution wherein the liquid particles have a mean diameter of less than 50 microns, and, preferably in the range of less than about 15 microns, e.g., in the 10-15 micron range, or less. Suitable means for generating such a fog include ultrasonic nebulizers, so-called "cold foggers" and thermal foggers (of the types sometimes used by disc jockeys at affairs). Alternatively, the solution-dispensing device 822 may be an atomizer of the type that uses a tube having a small orifice to blow air over a tube leading to the solution, whereby a venturi is created, much like a perfume atomizer. The benefit of such a fogger or atomizer, as contrasted to the wands having spray nozzles, is that the fog or fine mist produced by the dispensing device 822 will readily disburse over all sides of the coil 808 and can continue through the supply 806 to treat the interior portions of the ductwork remote from the coil.

Also shown in the embodiment illustrated in FIG. 8 is a sensor unit 826. Again, while only a single sensor unit 826 is depicted in FIG. 8, two or more sensor units can be employed in a given application of the invention 800. It is intended that the sensor units be capable of "sniffing" the air to detect anything that may be sensed. For example, a moisture-sensing unit could be used in the system 800 to enable the appropriate distribution of moisture to the air using a dispensing device 822. Generally, moisture is only added when the system 800 is in a heating, rather than cooling mode. The amount of moisture that is added to the air will be controlled based on the amount of moisture (e.g., the relative humidity) measured by the moisture sensor 826, and the control devices described herein may regulate it.

Similarly, a hazardous gas detector (e.g., to sense natural gas, carbon monoxide, radon, etc.) may be used as one of the sensors 826 in which case a local or remote alarm unit 828 could sound an alarm, or a display (either local or remote) could display the concentration of the undesirable gas. Other sensors, such as ionization or particle sensors could be used to detect, measure, and display (or alarm) based on fire, pollen, or other air contaminants, as may be desired.

In view of the invention's ability to combine sensors 826, dispensers 822, alarms 828, and local and remote displays, any number of air quality issues can be detected and dealt with by the invention 800.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including hand-held devices, smart phones, multiprocessor systems, microprocessor-based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the invention, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present invention may be embodied in hardware and/or in software (including firmware, resident software, microcode, etc.). In other words, embodiments of the present invention may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include an electrical connection having one or more wires, a portable computer diskette, a random access memory (RAM), a read only memory (ROM), an erasable programmable read only memory (EPROM or Flash memory), an optical fiber, and a portable compact disc read only memory (CD-ROM). Note that the computer-usable or computer-readable medium could even be paper or another suitable media, upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed method steps may be modified in any manner, including by reordering stages and/or inserting or deleting stages, without departing from the invention.

I claim:

1. Apparatus for cleaning an evaporator coil housed in a plenum of an air conditioner comprising:

(a) at least one reservoir adapted to hold a substance that can be used to remediate said evaporator coil;

(b) a pump configured to draw a metered amount of a substance from said at least one reservoir;

(c) at least one fogging device located within said plenum wherein said evaporator coil is located, said at least one fogging device being configured to cause a fog of said substance to be formed within said plenum;

(d) a controller configured to control the operation of said air conditioner, said pump, and said at least one fogging device, whereby said controller is configured to prevent operation of said air conditioner, to cause said pump to transfer said substance from said at least one reservoir to said at least one fogging device while operation of said air conditioner has been stopped, and to cause said at least one fogging device located within said plenum wherein said evaporator coil is located to cause a fog of said substance to be formed within said plenum, whereby a fog whose mean particle size is less than 50 microns will be produced that completely engulfs said evaporator coil as well as adjacent surfaces, after which said controller is adapted to resume operation of said air conditioner.

2. The apparatus of claim 1 wherein said at least one fogging device is selected to create a fog whose mean particle size is between 10 microns and 15 microns.

3. The apparatus of claim 1 wherein said at least one fogging device is selected from the group consisting of ultrasonic nebulizers, cold foggers, thermal foggers, ultrasonic foggers, and venturi-type atomizers.

4. The apparatus of claim 1 further comprising a user interface, adapted to permit a user to enter a time for said controlling device to perform a cleaning cycle, a length of time for said cleaning cycle, or a length of time for said controlling device to prevent the air conditioner from operating.

5. The apparatus of claim 1 wherein said substance in said at least one reservoir is selected to be a mixture of a fizzing agent, a working ingredient able to kill and break down mildew, a surfactant, and a carrier.

6. The apparatus of claim 5 wherein said substance is selected to be a mixture of a fizzing agent consists of hydrogen peroxide.

7. The apparatus of claim 6 wherein said working ingredient is grapefruit seed extract.

8. The apparatus of claim 7 wherein said surfactant is orange oil.

9. The apparatus of claim 8 wherein said carrier is water.

* * * * *